US00PP27377P2

(12) United States Plant Patent
Grazzini

(10) Patent No.: US PP27,377 P2
(45) Date of Patent: Nov. 15, 2016

(54) ***LANTANA* PLANT NAMED 'G12164'**

(50) Latin Name: *Lantana camara*
Varietal Denomination: G12164

(71) Applicant: Richard A. Grazzini, Bellefonte, PA (US)

(72) Inventor: Richard A. Grazzini, Bellefonte, PA (US)

(73) Assignee: GardenGenetics LLC, Bellefonte, PA (US)

( * ) Notice: Subject to any disclaimer, the term of this patent is extended or adjusted under 35 U.S.C. 154(b) by 163 days.

(21) Appl. No.: 14/121,811

(22) Filed: Oct. 20, 2014

(51) Int. Cl.
*A01H 5/02* (2006.01)

(52) U.S. Cl.
USPC ..... Plt./227

(58) Field of Classification Search
USPC ..... Plt./227
See application file for complete search history.

*Primary Examiner* — Keith Robinson
(74) *Attorney, Agent, or Firm* — C. A. Whealy

(57) ABSTRACT

A new and distinct cultivar of *Lantana* plant named 'G12164', characterized by its compact, upright and mounding plant habit; freely branching growth habit; dense and bushy plant form; small dark green-colored leaves; freely flowering habit; plants flower continuously throughout the summer; flowers that are initially bright yellow in color and with development become light yellow in color; flowers that do not produce fruits and seeds; and good garden performance.

1 Drawing Sheet

Botanical designation: *Lantana camara.*
Cultivar denomination: 'G12164'.

BACKGROUND OF THE INVENTION

The present invention relates to a new and distinct cultivar of *Lantana* plant, botanically known as *Lantana camara* and hereinafter referred to by the name 'G12164'.

The new *Lantana* plant is a product of a planned breeding program conducted by the Inventor in Bellefonte, Pa. The objective of the breeding program is to create new compact and freely-branching *Lantana* plants with attractive flower coloration.

The new *Lantana* plant originated from a cross-pollination made by the Inventor during the summer of 2011 in Bellefonte, Pa. of *Lantana camara* 'Balucyell', disclosed in U.S. Plant Pat. No. 14,684, as the female, or seed, parent with an unnamed seedling selection of *Lantana camara*, not patented, as the male, or pollen, parent. The new *Lantana* plant was discovered and selected by the Inventor as a single flowering plant from within the progeny of the stated cross-pollination in a controlled greenhouse environment in Bellefonte, Pa. on Feb. 23, 2012.

Asexual reproduction of the new *Lantana* plant by vegetative cuttings in a controlled greenhouse environment in Bellefonte, Pa. since May 16, 2012 has shown that the unique features of this new *Lantana* plant are stable and reproduced true to type in successive generations.

SUMMARY OF THE INVENTION

Plants of the new *Lantana* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'G12164'. These characteristics in combination distinguish 'G12164' as a new and distinct *Lantana* plant:

1. Compact, upright and mounding plant habit.
2. Freely branching growth habit; dense and bushy plant form.
3. Small dark green-colored leaves.
4. Freely flowering habit; plants flower continuously throughout the summer.
5. Flowers that are initially bright yellow in color and with development become light yellow in color.
6. Flowers that do not produce fruits and seeds.
7. Good garden performance.

Plants of the new *Lantana* can be compared to plants of the female parent, 'Balucyell'. Plants of the new *Lantana* differ primarily from plants of 'Balucyell' in the following characteristics:

1. Plants of the new *Lantana* are more compact than and not as vigorous as plants of 'Balucyell'.
2. Plants of the new *Lantana* are more upright than plants of 'Balucyell'.
3. Plants of the new *Lantana* are more freely branching and denser than plants of 'Balucyell'.
4. Plants of the new *Lantana* have smaller leaves than plants of 'Balucyell'.
5. Plants of the new *Lantana* and 'Balucyell' differ slightly in flower color.

Plants of the new *Lantana* can be compared to plants of the male parent selection. Plants of the new *Lantana* differ primarily from plants of the male parent selection in the following characteristics:

1. Plants of the new *Lantana* are more compact than and not as vigorous as plants of the male parent selection.
2. Plants of the new *Lantana* are more upright than plants of the male parent selection.

3. Plants of the new *Lantana* are more freely branching and denser than plants of the male parent selection.
4. Plants of the new *Lantana* and the male parent selection differ slightly in flower color.

Plants of the new *Lantana* can be compared to plants of the *Lantana* sp. 'Chapel Hill Yellow', disclosed in U.S. Plant Pat. No. 19,548. Plants of the new *Lantana* differ from plants of 'Chapel Hill Yellow' in the following characteristics:

1. Plants of the new *Lantana* are more compact than and not as vigorous as plants of 'Chapel Hill Yellow'.
2. Plants of the new *Lantana* are more upright than plants of 'Chapel Hill Yellow'.
3. Plants of the new *Lantana* are more freely branching and denser than plants of 'Chapel Hill Yellow'.
4. Plants of the new *Lantana* and 'Chapel Hill Yellow' differ slightly in flower color.
5. Plants of the new *Lantana* do not produce fruits and seeds whereas plants of 'Chapel Hill Yellow' produce fruits and seeds.

Plants of the new *Lantana* can also be compared to plants of the *Lantana camara* 'Robpwcrm', disclosed in U.S. Plant Pat. No. 19,347. Plants of the new *Lantana* differ from plants of 'Robpwcrm' in the following characteristics:

1. Plants of the new *Lantana* are more compact than and not as vigorous as plants of 'Robpwcrm'.
2. Plants of the new *Lantana* are more upright than plants of 'Robpwcrm'.
3. Plants of the new *Lantana* are more freely branching and denser than plants of 'Robpwcrm'.
4. Plants of the new *Lantana* and 'Robpwcrm' differ slightly in flower color.
5. Plants of the new *Lantana* do not produce fruits and seeds whereas plants of 'Robpwcrm' produce fruits and seeds.

BRIEF DESCRIPTION OF THE PHOTOGRAPHS

The accompanying colored photographs illustrate the overall appearance of the new *Lantana* plant showing the colors as true as it is reasonably possible to obtain in colored reproductions of this type. Colors in the photographs may differ slightly from the color values cited in the detailed botanical description which accurately describe the colors of the new *Lantana* plant.

The photograph at the bottom of the sheet comprises a side perspective view of a typical flowering plant of 'G12164' grown in a container.

The photograph at the top of the sheet is a close-up view of a typical flowering plant of 'G12164'.

DETAILED BOTANICAL DESCRIPTION

The aforementioned photographs and following observations and measurements describe plants grown during the spring in 11.5-cm containers in an outdoor nursery in Bonsall, Calif. and under commercial practices typical of commercial *Lantana* production. During the production of the plants, day temperatures ranged from 24° C. to 27° C., night temperatures ranged from 18° C. to 21° C. and light levels averaged 7,000 foot-candles. Plants were grown under long day/short night photoinductive conditions. Plants were pinched two times and were six weeks old when the photographs and the description were taken. In the following description, color references are made to The Royal Horticultural Society Colour Chart, 2007 Edition, except where general terms of ordinary dictionary significance are used.

Botanical classification: *Lantana camara* 'G12164'.

Parentage:

*Female, or seed, parent.*—*Lantana camara* 'Balucyell', disclosed in U.S. Plant Pat. No. 14,684.

*Male, or pollen, parent.*—Unnamed seedling selection of *Lantana camara,* not patented.

Propagation:

*Type.*—By vegetative cuttings.

*Time to initiate roots, summer.*—About ten days at temperatures about 22° C.

*Time to initiate roots, winter.*—About two weeks at temperatures about 22° C.

*Time to produce a rooted young plant, summer.*—About three weeks at temperatures about 22° C.

*Time to produce a rooted young plant, winter.*—About four weeks at temperatures about 22° C.

*Root description.*—Fibrous; medium in thickness.

*Rooting habit.*—Freely branching; medium density.

Plant description:

*Plant and growth habit.*—Compact, upright and mounding plant habit; moderately vigorous growth habit and moderate growth rate.

*Plant height.*—About 19 cm.

*Plant diameter.*—About 22 cm.

Lateral branch description:

*Branching habit.*—Freely branching habit with about five primary lateral branches developing per plant; each primary lateral branch with potentially two secondary lateral branches developing at every node; pinching enhances lateral branch development.

*Length.*—About 16 cm.

*Diameter.*—About 4 mm.

*Internode length.*—About 3 cm.

*Strength.*—Strong.

*Texture.*—Pubescent; minute; longitudinally ridged; woody towards the base.

*Color, young stems.*—Close to 146C.

*Color, mature stems.*—Close to 199B to 199C.

Leaf description:

*Arrangement.*—Opposite, simple.

*Length.*—About 5.6 cm.

*Width.*—About 2.8 cm.

*Shape.*—Elliptic.

*Apex.*—Acute.

*Base.*—Attenuate.

*Margin.*—Serrate.

*Texture, upper surface.*—Coarse and rough, leathery; glabrous.

*Texture, lower surface.*—Coarse and rough, leathery; pubescent, minute.

*Venation pattern.*—Pinnate; arcuate to reticulate.

*Color.*—Developing leaves, upper surface: Close to 137B. Developing leaves, lower surface: Close to 146B. Fully expanded leaves, upper surface: Close to N137A; venation, close to 146B. Fully expanded leaves, lower surface: Close to 146A; venation, close to 147C.

*Petiole length.*—About 1.2 cm.

*Petiole diameter.*—About 2 mm.

*Petiole texture, upper and lower surfaces.*—Pubescent, minute.

*Petiole color, upper surface.*—Close to 146B.

*Petiole color, lower surface.*—Close to 146B to 146C.

Flower description:

*Flower arrangement and flowering habit*.—Solitary tubular to somewhat salverform flowers arranged in terminal and axillary hemispherical umbels; flowers face mostly upward or outward; freely flowering habit with about 45 flowers developing per inflorescence and about nine inflorescences developing per lateral branch.

*Natural flowering season*.—Long flowering period; plants of the new *Lantana* flower continuously from spring until frost in Southern California; depending on temperatures, plants begin flowering about six to eight weeks after planting.

*Flower longevity on the plant*.—About two to three days; flowers not persistent.

*Fragrance*.—None detected.

*Inflorescence height*.—About 1.8 cm.

*Inflorescence diameter*.—About 3.6 cm.

*Flowers*.—Appearance: Flared trumpet, corolla fused, five-parted; sessile. Diameter: About 1 cm by 1.2 cm. Depth (height): About 2 cm. Throat diameter: Less than 1 mm. Tube diameter: About 1.5 mm. Tube length: About 1.5 mm.

*Flower buds*.—Length: About 1.2 cm. Diameter: About 3 mm. Shape: Tubular, narrow with rounded apex. Color: Close to 8A.

*Corolla*.—Arrangement: Single whorl of five fused petals. Petal lobe length: About 5 mm to 7 mm. Petal lobe width: About 4 mm to 6 mm. Petal lobe shape: Rounded. Petal lobe apex: Rounded, sinuate; curving upwardly. Petal margin: Mostly entire. Petal texture, upper and lower surfaces: Smooth, glabrous. Throat and tube texture: Pubescent. Color: When opening, upper surface: Close to 14B. When opening, lower surface: Close to 14C. Fully opened, upper surface: Close to 12A; color does not fade with development. Fully opened, lower surface: Close to 14C; color does not fade with development. Throat: Close to 2B. Tube: Close to 14C.

*Calyx*.—Appearance: Short and narrow tubular calyx with four fused sepals. Length: About 2 mm. Diameter: Less than 1 mm. Shape: Lanceolate. Sepal apex: Acute. Sepal margin: Entire. Sepal texture, inner surface: Smooth, glabrous. Sepal texture, outer surface: Pubescent, minute. Sepal color, inner surface: Close to 145D. Sepal color, outer surface: Close to 145C.

*Peduncles*.—Length: About 4.2 cm. Diameter: About 2 mm. Strength: Strong. Texture: Pubescent, minute. Color: Close to 146B.

*Reproductive organs*.—Stamens: Quantity and arrangement: Four per flower, adnate to floral tube. Filament length: About 2 mm. Filament color: Close to 153D. Anther length: Less than 1 mm. Anther shape: Oval. Anther color: Close to 163B. Pollen amount: None observed. Pistils: Quantity: One per flower. Pistil length: About 4 mm. Stigma shape: Round. Stigma color: Close to 145C. Style length: About 2 mm. Style color: Close to 145D. Ovary color: Close to 145C. Fruits and seeds: Fruit and seed development have not been observed on plants of the new *Lantana*.

Garden performance: Plants of the new *Lantana* have been observed to have good garden performance and to tolerate wind, rain and temperatures ranging from about −3° C. to about 35° C.

Pathogen & pest tolerance: Plants of the new *Lantana* have not been observed to be tolerant to pests and pathogens common to *Lantana* plants.

It is claimed:

1. A new and distinct *Lantana* plant named 'G12164' as illustrated and described.

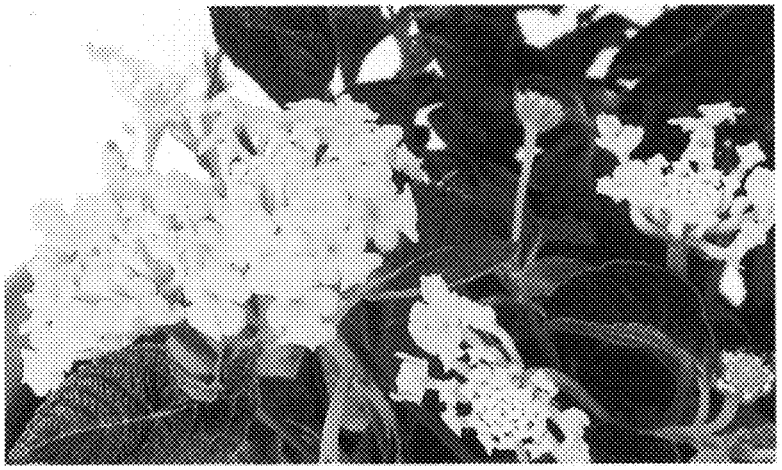
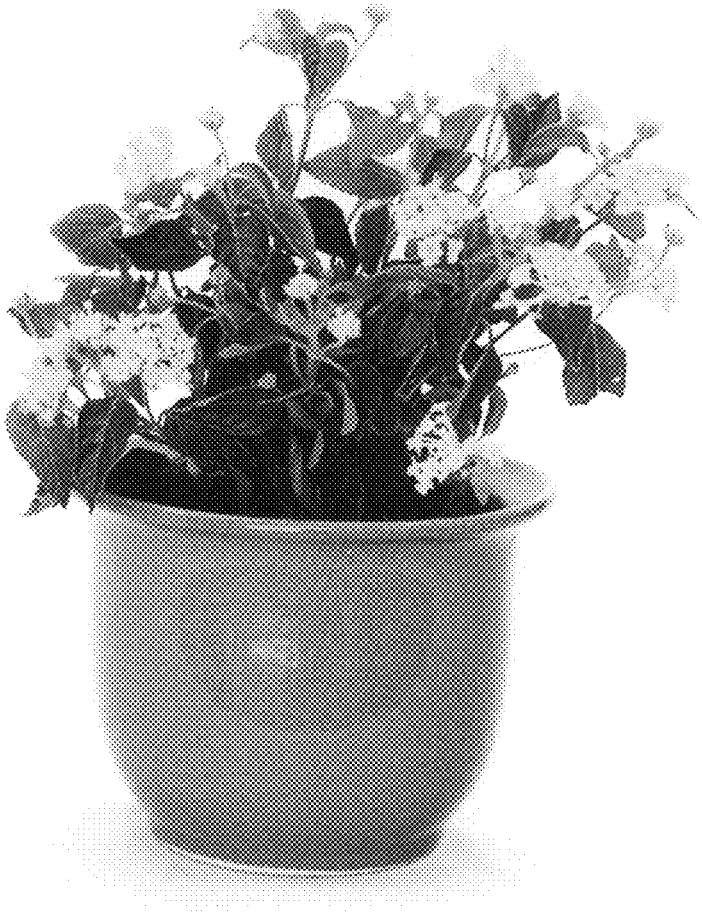

* * * * *